United States Patent [19]

Fujiu et al.

[11] Patent Number: 4,966,891
[45] Date of Patent: Oct. 30, 1990

[54] FLUOROCYTIDINE DERIVATIVES

[75] Inventors: Morio Fujiu, Chigasaki; Hideo Ishitsuka, Yokohama; Masanori Miwa, Kamakura; Isao Umeda, Yokohama; Kazuteru Yokose, Urayasu, all of Japan

[73] Assignee: Hoffmann-La Roche Inc., Nutley, N.J.

[21] Appl. No.: 268,437

[22] Filed: Nov. 8, 1988

[30] Foreign Application Priority Data

Nov. 17, 1987 [EP] European Pat. Off. ........ 87116926.4

[51] Int. Cl.$^5$ .................... C07H 19/06; A61K 31/505
[52] U.S. Cl. ......................................... 514/49; 536/23
[58] Field of Search ............... 536/22, 23, 24; 514/49, 514/274

[56] References Cited

U.S. PATENT DOCUMENTS

| | | | |
|---|---|---|---|
| 3,404,144 | 10/1968 | Fox et al. | 536/23 |
| 4,071,680 | 1/1978 | Cook | 536/22 |
| 4,122,251 | 10/1978 | Misaki et al. | 536/23 |
| 4,659,698 | 4/1987 | Imbach et al. | 536/23 |
| 4,816,569 | 3/1989 | Miyoshi | 536/23 |

OTHER PUBLICATIONS

Briggle et al., Chem. Abs. 105:218184w (1986).
Cook et al., Journal of Medicinal Chem. vol. 22, 1330-6, (1979) "Fluorinated Pyrimidine Nucleosides . . . ".
Matsuda et al., Chem. Pharm. Bull. 33(6) 2575-2578, (1985) "Reaction of Uracil Nucleosides with . . . ".

Primary Examiner—Cecilia Shen
Attorney, Agent, or Firm—George M. Gould; William H. Epstein; Patricia S. Rocha

[57] ABSTRACT

The novel 5'-deoxy-5-fluorocytidine derivatives of formula

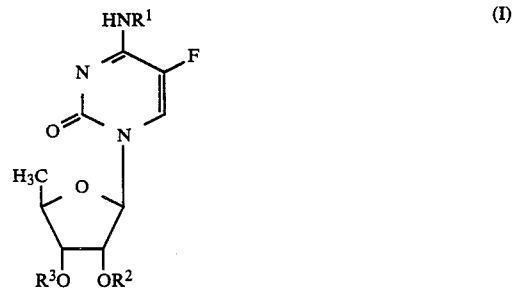

wherein $R^1$, $R^2$ and $R^3$ are hydrogen or an easily hydrolyzable radical under physiological conditions, with the proviso that, at least one or $R^1$, $R^2$ and $R^3$ is an easily hydrolyzable radical under physiological conditions, as well as hydrates of solvates of these compounds have antitumor properties. They can be prepared from compounds of formula I, wherein $R^1$ is hydrogen or an amino-protecting radical and $R^2$ and $R^3$ are hydrogen or a hydroxy-protecting radical or taken together are a cyclic hydroxy-protecting radical.

7 Claims, No Drawings

FLUOROCYTIDINE DERIVATIVES

The present invention is concerned with novel 5'-deoxy-5-fluorocytidine derivatives, a process for their manufacture and an antitumor agent containing said derivatives.

More particularly, the present invention is concerned with novel 5'-deoxy-5-fluorocytidine derivatives represented by the general formula (I),

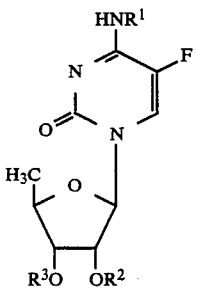

wherein $R^1$, $R^2$ and $R^3$ independently represent a hydrogen atom or an easily hydrolyzable radical under physiological conditions, with the proviso that, at least one of the radicals represented by the symbol $R^1$, $R^2$ or $R^3$ represents an easily hydrolyzable radical under physiological conditions, as well as hydrates or solvates of the compounds of the general formula (I), which are useful as effective ingredients for antitumor agents.

In the general formula (I) above "easily hydrolyzable radical under physiological conditions" preferably is a radical represented by the formula, $$R^4CO-, R^5OCO- \text{ or } R^6SCO-$$

wherein $R^4$ represents a hydrogen atom, an alkyl, cycloalkyl, oxoalkyl, alkenyl, aralkyl or aryl radical, and $R^5$ and $R^6$ represent an alkyl or aralkyl radical.

As used in this specification, the term "alkyl" refers to straight or branched chain having 1 to 19 carbon atoms selected from the group consisting of methyl, ethyl, propyl, isopropyl, butyl, isobutyl, sec-butyl, tert-butyl, pentyl, isopentyl, neopentyl, hexyl, isohexyl, heptyl, octyl, nonyl, decyl, undecyl, dodecyl, tridecyl, tetradecyl, pentadecyl, hexadecyl, heptadecyl and nonadecyl.

The term "cycloalkyl" as used herein is a member selected from the group consisting of cyclopropyl, cyclobutyl, cyclopentyl, cyclohexyl and adamantyl.

The term "oxoalkyl" is a member selected from the group consisting of acetyl, propionyl, butyryl, 2-oxopropyl, 2-oxobutyl and 3-oxobutyl.

The term "alkenyl" means an unsubstituted or substituted alkenyl radical having 3 to 19 carbon atoms selected from the group consiting of allyl, butenyl, 3-methyl-2-butenyl, 1-methyl-2-propenyl, hexenyl, decenyl, undecenyl, tridecenyl, pentadecenyl, heptadecenyl, heptadecadienyl, heptadecatrienyl, nonadecenyl, nonadecadienyl, nonadecatetraenyl and 2-phenylvinyl.

The term "aralkyl" means an unsubstituted or substituted aralkyl radical selected from the group consisting of benzyl, 1-phenylethyl, methylbenzyl, fluorobenzyl, chlorobenzyl, methoxybenzyl, dimethoxybenzyl, nitrobenzyl, phenethyl, picolyl and 3-indolylmethyl.

The term "aryl" means an unsubstituted or substituted aryl radical such as phenyl, tolyl, xylyl, mesityl, cumenyl, ethylphenyl, fluorophenyl, chlorophenyl, bromophenyl, iodophenyl, difluorophenyl, dichlorophenyl, methoxyphenyl, dimethoxyphenyl, trimethoxyphenyl, ethoxyphenyl, diethoxyphenyl, triethoxyphenyl, propoxyphenyl, methylenedioxyphenyl, (methylthio)phenyl, nitrophenyl, cyanophenyl, acetylphenyl, carbamoylphenyl, methoxycarbonylphenyl, naphthyl, biphenylyl, thienyl, methylthienyl, furyl, nitrofuryl, pyrrolyl, methylpyrrolyl, imidazolyl, pyrazoly-1, pyridyl, methylpyridyl and pyrazinyl.

Particularly preferred 5'-deoxy-5-fluorocytidine derivatives provided by the present invention are:

$N^4$-acetyl-5'-deoxy-5-fluorocytidine,
5'-deoxy-5-fluoro-$N^4$-propionylcytidine,
$N^4$-butyryl-5'-deoxy-5-fluorocytidine,
5'-deoxy-5-fluoro-$N^4$-isobutyrylcytidine,
5'-deoxy-5-fluoro-$N^4$-(2-methylbutyryl)cytidine,
5'-deoxy-$N^4$-(2-ethylbutyryl)-5-fluorocytidine,
5'-deoxy-$N^4$-(3,3-dimeth.lbyutyryl)-5-fluorocytidine,
5'-deoxy-5-fluoro-$N^4$-pivaloylcytidine,
5'-deoxy-5-fluoro-$N^4$-valerylcytidine,
5'-deoxy-5-fluoro-$N^4$-isovalerylcytidine,
5'-deoxy-5-fluoro-$N^4$-(2-methylvaleryl)cytidine,
5'-deoxy-5-fluoro-$N^4$-(3-methylvaleryl)cytidine,
5'-deoxy-5-fluoro-$N^4$-(4-methylvaleryl)cytidine,
5'-deoxy-5-fluoro-$N^4$-hexanoylcytidine,
5'-deoxy-5-fluoro-$N^4$-heptanoylcytidine,
5'-deoxy-5-fluoro-$N^4$-octanoylcytidine,
5'-deoxy-5-fluoro-$N^4$-nonanoylcytidine,
5'-deoxy-5-fluoro-$N^4$-hexadecanoylcytidine,
$N^4$-benzoyl-5'-deoxy-5-fluorocytidine,
5'-deoxy-5-fluoro-$N^4$-(4-methylbenzoyl)cytidine,
5'-deoxy-5-fluoro-$N^4$-(3-methylbenzoyl)cytidine,
5'-deoxy-5-fluoro-$N^4$-(2-methylbenzoyl)cytidine,
5'-deoxy-$N^4$-(4-ethylbenzoyl)-5-fluorocytidine,
5'-deoxy-$N^4$-(3,4-dimethylbenzoyl)-5-fluorocytidine,
5'-deoxy-$N^4$-(3,5-dimethylbenzoyl)-5-fluorocytidine,
5'-deoxy-5-fluoro-$N^4$-(4-methoxybenzoyl)cytidine,
5'-deoxy-$N^4$-(3,4-dimethoxybenzoyl)-5-fluorocytidine,
5'-deoxy-$N^4$-(3,5-dimethoxybenzoyl)-5-fluorocytidine,
5'-deoxy-5-fluoro-$N^4$-(3,4,5-trimethoxybenzoyl)cytidine,
5'-deoxy-5-fluoro-$N^4$-(3,4,5-triethoxybenzoyl)cytidine,
5'-deoxy-$N^4$-(4-ethoxybenzoyl)-5-fluorocytidine,
5'-deoxy-5-fluoro-$N^4$-(4-propoxybenzoyl)cytidine,
5'-deoxy-$N^4$-(3,5-diethoxybenzoyl)-5-fluorocytidine,
$N^4$-(4-chlorobenzoyl)-5'-deoxy-5-fluorocytidine,
5'-deoxy-$N^4$-(3,4-dichlorobenzoyl)-5-fluorocytidine,
5'-deoxy-$N^4$-(3,5-dichlorobenzoyl)-5-fluorocytidine,
5'-deoxy-5-fluoro-$N^4$-(4-nitrobenzoyl)cytidine,
5'-deoxy-5-fluoro-$N^4$-(4-methoxycarbonylbenzoyl)cytidine,
$N^4$-(4-acetylbenzoyl)-5'-deoxy-5-fluorocytidine,
5'-deoxy-5-fluoro-$N^4$-(phenylacetyl)cytidine,
5'-deoxy-5-fluoro-$N^4$-(4-methoxyphenylacetyl)cytidine,
5'-deoxy-5-fluoro-$N^4$-nicotinoylcytidine,
5'-deoxy-5-fluoro-$N^4$-isonicotinoylcytidine,
5'-deoxy-5-fluoro-$N^4$-picolinoylcytidine,
5'-deoxy-5-fluoro-$N^4$-(2-furoyl)cytidine,
5'-deoxy-5-fluoro-$N^4$-(5-nitro-2-furoyl)cytidine,
5'-deoxy-5-fluoro-$N^4$-(2-thenoyl)cytidine,
5'-deoxy-5-fluoro-$N^4$-(5-methyl-2-thenoyl)cytidine,
5'-deoxy-5-fluoro-$N^4$-(1-methyl-2-pyrrolecarbonyl)cytidine,
5'-deoxy-5-fluoro-$N^4$-(3-indolylacetyl)cytidine,
$N^4$-(3-butenoyl)-5'-deoxy-5-fluorocytidine, 5'-O-benzoyl-5'-deoxy-5-fluorocytidine,
N⁴,3'-O-dibenzoyl-5'-deoxy-5-fluorocytidine and
5'-deoxy-N⁴-(ethylthio)carbonyl-5-fluorocytidine.

Further preferred 5'-deoxy-5-fluorocytidine derivatives provided by the present invention are:
5'-deoxy-5-fluoro-N⁴-octadecanoylcytidine,
N⁴-cyclopropanecarbonyl-5'-deoxy-5-fluorocytidine,
N⁴-cyclohexanecarbonyl-5'-deoxy-5-fluorocytidine,
N⁴-(1-adamantanecarbonyl)-5'-deoxy-5-fluorocytidine,
5'-deoxy-5-fluoro-N⁴-(2-methoxybenzoyl)cytidine,
5'-deoxy-N⁴-(2,4-dimethoxybenzoyl)-5-fluorocytidine,
5'-deoxy-5-fluoro-N⁴-piperonyloylcytidine,
5'-deoxy-5-fluoro-N⁴-(4-fluorobenzoyl)cytidine,
N⁴-(2-chlorobenzoyl)-5'-deoxy-5-fluorocytidine,
N⁴-(3-chlorobenzoyl)-5'-deoxy-5-fluorocytidine,
5'-deoxy-5-fluoro-N⁴-(3-nitrobenzoyl)cytidine,
5'-deoxy-5-fluoro-N⁴-[4-(methylthio)benzoyl]cytidine,
5'-deoxy-5-fluoro-N⁴-(2-naphthoyl)cytidine,
5'-deoxy-5-fluoro-N⁴-(3-furoyl)cytidine,
5'-deoxy-5-fluoro-N⁴-(3-phenylpropionyl)cytidine,
N⁴-cinnamoyl-5'-deoxy-5-fluorocytidine,
2',3'-di-O-benzoyl-5'-deoxy-5-fluorocytidine,
N⁴,2'-O,3'-O-tribenzoyl-5'-deoxy-5-fluorocytidine,
5'-deoxy-5-fluoro-N⁴-(octyloxycarbonyl)cytidine,
N⁴-(benzyloxycarbonyl)-5'-deoxy-5-fluorocytidine and
5'-deoxy-5-fluoro-N⁴-formylcytidine.

The novel 5'-deoxy-5-fluorocytidine derivatives represented by the general formula (I) as well as hydrates or solvates of the compounds of the general formula (I) are manufactured in accordance with the present invention by a process which comprises a reaction of a compound represented by the general formula (II).

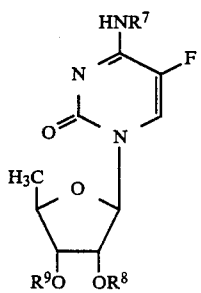

(II)

wherein
R⁷ represents a hydrogen atom or an amino-protecting radical, R⁸ and R⁹ are independently a hydrogen atom or a hydroxyprotecting radical, or R⁸ and R⁹, taken together, may form a cyclic hydroxy-protecting radical.
with a compound represented by the general formula (III).

 XCOR⁴ (III)

wherein X represents a leaving radical and R⁴ represents a hydrogen atom, an alkyl, cycloalkyl, oxoalkyl, alkenyl, aralkyl or aryl radical,
Or with a compound represented by the general formula (IV),

 YCOR¹⁰ (IV)

wherein Y represents a halogen atom and R¹⁰ represents a radical represented by the formula,

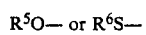 R⁵O— or R⁶S— in which R⁵ and R⁶ represent an alkyl or aralkyl radical, followed, if necessary by removal of a protecting radical.

The term "amino-protecting radical" means such as benzyloxycarbonyl, phenoxycarbonyl, 2,2,2-trichloroethoxycarbonyl, ethoxycarbonyl, tert-butyloxycarbonyl and trifluoroacetyl. The term "hydroxy-protecting radical" means e.g. benzyl, methoxybenzyl, trimethylsilyl, triethylsilyl, isopropyldimethylsilyl, tert-butyldimethylsilyl, tert-butyldiphenylsilyl, thexyldimethylsilyl, allyl, methoxymethyl, (2-methoxyethoxy)methyl and tetrahydropyranyl. The term "cyclic hydroxy-protecting radical" means e.g. cyclic acetal, cyclic ketal, cyclic carbonate, cyclic ortho ester and cyclic 1,3-(1,1,3,3-tetraisopropyl)disiloxanediyl. The term "leaving radical" means e.g. halogen atom, acyloxy, alkyloxycarbonyloxy, succinimidooxy, phthalimidooxy, 4-nitrophenyl. azido, 2,4,6-triisopropylbenzenesulfonyl and diethyloxyphosphoryloxy. The term "halogen atom" as used herein represents chloro, bromo or iodo.

Among the compounds represented by the general formula (II). 5'-deoxy-5-fluorocytidine is a known compound [J. Med. Chem., 22, 1330 (1979)] and other compounds represented by the general formula (II) can be prepared from 5'-deoxy-5-fluorocytidine by the procedures known to those skilled in the art. or from 5'-deoxy-5-fluorouridine by the procedures described in the literature [Chem. Pharm. Bull., 33, 2575 (1985)].

The compounds of the formula (III) used in the above reaction are acid halides, acid anhydrides, mixed anhydrides
[Prepared by a reaction of R⁴CO₂H with 2,4,6-triisopropylbenzenesulfonyl chloride or diethyl chlorophosphate (wherein R⁴ is the same as defined above)], activated esters (such as N-hydroxysuccinimide esters. N-hydroxyphthalimide esters. 4-nitrophenyl esters and the like), acyl azides or mixed carbonic anhydrides.

The compounds of the formula (IV) used in the above reaction are alkyloxycarbonyl halides, aralkyloxycarbonyl halides, (alkylthio)carbonyl halides or (aralkylthio)carbonyl halides.

The reaction of the compound of the general formula (II) with the compound of the general formula (III) or (IV) can be carried out in a solvent such as pyridine, dioxane, tetrahydrofuran, acetonitrile, chloroform, dichloromethane, methanol, ethanol or water. Mixture of two or more solvents may also be used. The reaction can be carried out in the presence of an acid acceptor such as triethylamine, pyridine, picoline, dimethylaminopyridine, lutidine, N,N-dimethylaniline or an alkali metal hydroxide, carbonate or phosphate. The reaction temperature in the above reaction may be varied within a relatively wide range. In general. the reaction is carried out at a temperature between about 0° C. and 120° C. preferably between 0° C. and 50° C. In carrying out the reaction, 1, 2 or 3 moles or excess moles of the compound of the formula (III) or (IV) per mole of the compound of the formula (II) is employed.

The protecting radical may, if necessary, be removed after the reaction by procedures known to those skilled in the art.

The compounds provided by the present invention prepared in the above process may be isolated and purified by conventional techniques such as evaporation, filtration, extraction, precipitation, chromatography, recrystallization and a combination thereof.

The compounds of the formula (I) can exist in unsolvated as well as solvated forms, including hydrated forms. The hydration can be effected in the course of the manufacturing process or can occur gradually as a result of hygroscopic properties of an initially anhydrous product. For the controlled manufacture of a hydrate a completely or partially anhydrous product can be exposed to a moist atmosphere (e.g. at about 10° C. to 40° C.). Solvates with pharmaceutically acceptable solvents such as ethanol can be obtained during, for example, crystallization.

5'-deoxy-5-fluorocytidine derivatives represented by the general formula (I) as well as hydrates or solvates of the compounds of the general formula (I) prepared by the present invention exhibit activity against Sarcoma 180, Meth A fibrosarcoma and Lewis lung carcinoma in mice over a very wide range of dosages both orally and parenterally and are useful as antitumor agents. In general 5-fluorouracil and its derivatives cause intestinal toxicities and immunosuppressive toxicities, which are their major and dose limiting toxicities, 5'-deoxy 5-fluorocytidine derivatives in the present invention. are much improved in safety. When orally administered, they cause much less toxicity to intestinal tracts and immune systems than 5-fluorouracil (J.A.C.S. 79, 1957, 4559) and its typical prodrugs. tegafur: uracil=1:4 (UFT) and 5'-deoxy-5-fluorouridine (US 4071680). Therefore, the compounds provided by the present invention can be effectively utilized for the treatment of various tumors in human beings.

The present invention further relates to the pharmaceutical compositions containing one or more compounds of the present invention.

The compounds of the present invention can be administered orally or non-orally to human beings by various conventional administration methods. Moreover, the compounds according to the present invention are used singly or formulated with a compatible pharmaceutical carrier material. This carrier material can be an organic or inorganic inert carrier material suitable for enteral, percutaneous or parenteral administration such as, water, gelatin, gum arabic, lactose, starch, magnesium stearate, talc, vegetable oils, polyalkyleneglycols or petroleum jelly. The pharmaceutical preparations can be made up in a solid form (e.g. as tablets, dragees, enteric coating tablets, granulars, enteric coating granulars, suppositories, capsules or enteric capsules) in a semi-solid form (e.g. as salves) or in a liquid form (e.g. as solutions, suspensions or emulsions). The pharmaceutical preparations may be sterilised and/or may contain further adjuvants such as preserving, stabilizing, setting or emulsifying agents, flavour-improving agents, salts for variation of the osmotic pressure or substances acting as buffers. The pharmaceutical preparations can be prepared in a conventional manner.

The compounds according to the present invention can be used alone or as mixtures of two or more different compounds and the amount of the compounds is about 0.1 to 99.5%, preferably 0.5 to 95% based on the weight of the medicinal composition.

The medicinal composition according to the present invention may be formulated in a combination of the compound or compounds of the present invention with other conventional compounds which are pharmaceutically active.

A dosage per day to a patient of the novel 5'-deoxy-5-fluorocytidine derivatives of the present invention may be varied depending upon his weight and a state to be remedied. but generally is in the range of 0.5 to 700 mg per 1 kg of weight. preferably about 3 to 500 mg.

The antitumor a tivities of the compounds of the present invention are shown as follows:

Antitumor testino against Sarcoma 180

Sarcoma 180 cells ($2 \times 10^6$ cells) were implanted subcutaneously into mice (20-22 g) on day 0. The compounds of the present invention were administered daily from day 1 through 7 orally. The animals were sacrificed on day 14 and tumors were excised and weighed. The percent inhibition of tumor growth given in Table 1 below was calculated from the formula:

% Inhibition = $(1 - T/C) \times 100$

T = weight of the tumors from the treated group,
C = weight of the tumors from the control group.

TABLE 1

| Antitumor activity against Sarcoma 180 in mice | | |
|---|---|---|
| Compound (Example No.) | Dose × 7 (mmole/kg/day) | Inhibition (%) |
| 1 | 1.1 | 56 |
|   | 2.2 | 83 |
| 2 | 1.5 | 84 |
|   | 3.0 | 91 |
| 5 | 1.1 | 62 |
|   | 2.2 | 82 |
| 6 | 0.5 | 28 |
|   | 1.5 | 76 |
| 7 | 1.4 | 57 |
|   | 2.7 | 84 |
| 8 | 1.4 | 20 |
|   | 2.7 | 77 |
| 9 | 1.4 | 76 |
|   | 2.7 | 96 |
| 10 | 1.5 | 74 |
|    | 3.0 | 97 |
| 11 | 0.8 | 69 |
|    | 1.5 | 90 |
| 12 | 0.8 | 40 |
|    | 1.5 | 73 |
| 13 | 0.8 | 28 |
|    | 1.5 | 66 |
| 15 | 0.8 | 47 |
|    | 1.5 | 62 |
| 17 | 1.3 | 75 |
|    | 2.6 | 92 |
| 24 | 1.5 | 63 |
|    | 3.0 | 94 |
| 41 | 0.5 | −18 |
|    | 1.5 | 36 |
| 42 | 0.5 | 0 |
|    | 1.5 | 36 |

Antitumor testing against Meth A fibrosarcoma

Meth A fibrosarcoma cells ($2 \times 10^5$ cells) were implanted subcutaneously into mice (21-22 g). The testing against Meth A fibrosarcoma and the calculation of the percent inhibition of tumor growth were effected according to a manner analogous to that of the testing against Sarcoma 180. The results are shown in Table 2.

The comparative study on antitumor activity of a representative compound (Example 3) of the present invention with 5'-deoxy-5-fluorouridine was performed according to a manner analogous to that of the antitumor testing against Meth A fibrosarcoma. The results of this experiment and the fecal observation of Day 8 are shown in Table 3. They indicate that the compound of Example 3 is more potent in the antitumor activity but less toxic than 5'-deoxy-5-fluorouridine. In the same experiment the compound of Example 3 did not cause diarrhea, which is the dose limiting factor of 5'-deoxy-5-fluorouridine.

TABLE 2

Antitumor activity against Meth A fibrosarcoma in mice

| Compound (Example No.) | Dose × 7 (mmole/kg/day) | Inhibition (%) |
|---|---|---|
| 1 | 1.5 | 50 |
|   | 3.0 | 72 |
| 3 | 1.5 | 86 |
|   | 3.0 | 79 |
| 14 | 1.5 | 66 |
|   | 3.0 | 94 |
| 16 | 0.8 | 38 |
|   | 1.5 | 58 |
| 18 | 1.5 | 51 |
|   | 3.0 | 91 |
| 19 | 1.5 | 3 |
|   | 3.0 | 64 |
| 20 | 1.5 | 53 |
|   | 3.0 | 84 |
| 21 | 0.8 | 17 |
|   | 1.5 | 60 |
| 22 | 1.5 | 42 |
|   | 3.0 | 42 |
| 23 | 0.8 | 56 |
|   | 1.5 | 64 |
| 25 | 1.5 | −6 |
|   | 3.0 | 34 |
| 26 | 1.5 | 37 |
|   | 3.0 | 58 |
| 27 | 1.5 | 58 |
|   | 3.0 | 91 |
| 28 | 1.5 | −13 |
|   | 3.0 | −13 |
| 29 | 1.5 | 49 |
|   | 3.0 | 92 |
| 30 | 1.5 | 55 |
|   | 3.0 | 58 |
| 31 | 1.5 | 55 |
|   | 3.0 | 84 |
| 34 | 1.3 | 75 |
|   | 2.6 | 92 |
| 36 | 1.5 | 53 |
|   | 3.0 | 92 |
| 37 | 1.5 | 59 |
|   | 3.0 | 86 |
| 40 | 0.8 | 41 |
|   | 1.5 | 57 |
| 44 | 1.5 | 38 |
|   | 3.0 | 66 |
| 45 | 1.5 | 49 |
|   | 3.0 | 71 |
| 46 | 1.5 | 51 |
|   | 3.0 | 66 |
| 47 | 1.5 | 29 |
|   | 3.0 | 59 |
| 48 | 0.8 | 42 |
|   | 1.5 | 72 |
| 49 | 1.5 | 58 |
|   | 3.0 | 76 |
| 52 | 0.8 | 41 |
|   | 1.5 | 51 |
| 53 | 1.5 | 48 |
|   | 3.0 | 85 |
| 54 | 1.5 | 55 |
|   | 3.0 | 85 |
| 57 | 1.5 | 28 |

TABLE 2-continued

Antitumor activity against Meth A fibrosarcoma in mice

| Compound (Example No.) | Dose × 7 (mmole/kg/day) | Inhibition (%) |
|---|---|---|
|   | 3.0 | 56 |
| 59 | 1.5 | 23 |
|   | 3.0 | 80 |

TABLE 3

Antitumor activity against Meth A fibrosarcoma in mice and the fecal observation on Day 8

| Compound (Example No.) | Dose × 7 (mmole/kg/day) | Inhibition (%) | Fecal observation* |
|---|---|---|---|
| 3 | 0.4 | −27 | N |
|   | 0.8 | 20 | N |
|   | 1.5 | 86 | N |
|   | 3.0 | 79 | N |
| 5'-deoxy-5-fluorouridine | 0.4 | 34 | N |
|   | 0.8 | 31 | N |
|   | 1.5 | 66 | L–D |
|   | 3.0 | toxic | D |

*Fecal observation
N: normal feces
L: loose feces
D: diarrhea

Comparative antitumor testing against Lewis lung carcinoma

Antitumor activity of a representative compound (Example 1), of the present invention, was compared with that of 5'-deoxy-5-fluorouridine and a combination drug, UFT (tegafur: uracil =1:4). Mice were inoculated subcutaneously with Lewis lung carcinoma ($10^6$ cells) on day 0.

The compounds were administered daily for 14 times from day 1 by the p.o. route. The effective dose ($ED_{50}$) at which tumor growth was inhibited by 50%, and toxic doses were determined. Therapeutic indices (toxic doses/$ED_{50}$) obtained from the experiments are shown in Table 4. As Table 4 shows, the compound of the present invention has higher therapeutic indices than typical prodrugs of 5-fluorouracil, 5'-deoxy-5-fluorouridine and UFT. It caused less toxicity to intestinal tracts (diarrhea) and to immunoresponsible organs (thymus and bone marrow). These indicate that the compound provided by the present invention has a higher safety potential.

TABLE 4

| | Therapeutic Indices - Toxic Doses/$ED_{50}$* | | | |
|---|---|---|---|---|
| Compound (Example No.) | Max. Dose causing no diarrhea (A)** | Body weight gain: 10% reduction (B)** | 50% Thymus Shrinkage (C)** | 50% reduction No. of bone marrow cells (D)** |
| 1 | >13 | >13 | 11.3 | 10.7 |
| 5'-deoxy-5-fluorouridine | 5 | 6.4 | 5–10 | 5–10 |
| UFT | 1.5 | 2.5 | 1.1 | 1.5–2.9 |

*$ED_{50}$s of the compound, Example No. 1, 5'-deoxyo-5-fluorouridine and UFT measured at 15 days after the tumor inoculation were 0.15, 0.20 and 0.086 mmol/kg/day, respectively.
**Toxicities were measured at Day 10(A), 7(B), 14(C) and 14(D).

Comparative antitumor testing against Sarcoma 180, Meth A fibrosarcoma and UV 2237 fibrosarcoma The antitumor efficacy of the representative compound (Example 1) of the present invention in three murine tumor models was compared with that of 5'-deoxy-5-fluorouridine and 5'-deoxy-5-fluorocytidine. Mice were inoculated subcutaneously with Sarcoma 180, Meth A fibrosarcoma and UV 2237 fibrosarcoma, respectively at Day 0. The mice were then orally administered with the compounds daily for 7 times from Day 1. The efficacy was expressed as therapeutic indices ($ED_{max}/ED_{50}$) measured at Day 14 after the tumor inoculation, where $ED_{max}$ is a dose showing maximum inhibition of tumor growth. Results obtained from experiments are shown in Table 5.

TABLE 5

Comparative antitumor activity against Sarcoma 180, Meth A fibrosarcoma and UV 2237 fibrosarcoma.

| Compound (Example No.) | Therapeutic Indices | | |
|---|---|---|---|
| | S180 | Meth A | UV 2237 |
| 1 | 2.3 | 2.0 | 4.8 |
| 5'-deoxy-5-fluorocytidine | 2.0 | 1.2 | 1.0 |
| 5'-deoxy-5-fluorouridine | 2.4 | 1.1 | 1.6 |

Acute toxicity

The acute toxicity ($LD_{50}$) of the representative compound (Example 1, 5, 9, 24, 34, 46 and 47) of the present invention was examined by oral administration in mice. The respective $LD_{50}$ values obtained from experiments are more than 2,000 mg/kg.

The following examples illustrate the preferred methods for the preparation of the compounds of the present invention.

REFERENCE EXAMPLE (a) 5'-Deoxy-5-fluorocytidine (245 mg). tert-butyldimethylsilyl chloride (354 mg) and imidazole (284 mg) were dissolved in dimethylformamide (1.5 ml). The mixture was stirred for 18 hours at room temperature under nitrogen atmosphere. The reaction mixture was then poured into water and extracted with ethyl acetate. The extract was washed with water, dried over anhydrous sodium sultate and concentrated under reduced pressure to give 2',3'-bis-O-(tert-butyldimethylsilyl)-5'-deoxy-5-fluorocytidine (431 mg), MS 473 (M+).

(b) A solution of 5'-deoxy-5-fluorocytidine (490 mg), p-toluenesulfonic acid monohydrate (418 mg) and 2,2-dimethoxypropane (984 μl) in acetone (10 ml) was stirred for 1.5 hour at room temperature. To the solution was added sodium hydrogen carbonate (900 mg) and the mixture was stirred for 4 hours at room temperature. The precipitate was filtered off and washed with acetone. The combined filtrate was concentrated under reduced pressure. The residue was purified by silica gel column chromatography (dichloromethane-methanol) to give 5'-deoxy-5-fluoro-2',3'-O-isopropylidenecytidine (570 mg). MS 286 (MH+); mp of the picrate 169°~171° C.

EXAMPLE 1

1(a) 2',3'-Bis-O-(tert-butyldimethylsilyl)-5'-deoxy-5-fluorocytidine (9.46 g) obtained in Reference example (a), n-butyric anhydride (3.48 g) and 4-dimethylaminopyridine (2.93 g) were dissolved in methylenechloride (150 ml). The mixture was stirred overnight, then washed with water, dried over anhydrous sodium sulfate and concentrated under reduced pressure to give $N^4$-butyryl-2',3'-bis-O-(tert-butyldimethylsilyl)-5'-deoxy-5-fluorocytidine (9.75 g), MS 544 (MH+).

1(b) The product of Example 1(a) (9.75 g) was dissolved in tetrahydrofuran (80 ml) containing 80 mmole of tetrabutylammonium fluoride. The reaction mixture was stirred for 1.5 hours at room temperature. After removal of the solvent under reduced pressure, the residue was purified by silica gel column chromatography (ethyl acetate-methanol) followed by recrystallization from methanol to give $N^4$-butyryl-5'-deoxy-5-fluorocytidine (4.5 g). mp 156°~157° C.; MS 316 (MH+).

The following compounds were obtained according to a manner analogous to that of Example 1:

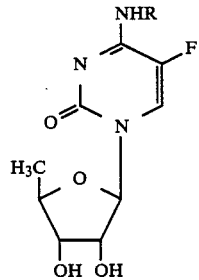

| Example No. | R | Melting point °C. | Recrystallization solvent | MS |
|---|---|---|---|---|
| 2 | —COCH3 | 157~159 | EtOH | 288 (MH+) |
| 3 | —CO—(C6H2)(OCH3)3 | 170~171 | EtOAc—Et2O | 440 (MH+) |

EXAMPLE 4

4(a) 2',3'-Bis-O-(tert-butyldimethylsilyl)-5'-deoxy-5-fluorocytidine (14.19 g) obtained in Reference example (a) was dissolved in dry pyridine (150 ml). To the solution was added dropwise n-butyryl chloride (3.84 g)

with stirring. The reaction mixture was stirred overnight. Pyridine was removed under reduced pressure and the residue was partitioned between water and ethyl acetate. The ethyl acetate layer was washed with water, dried over anhydrous sodium sulfate and concentrated under reduced pressure. The residue was purified by silica gel column chromatography (n-hexane - ethyl acetate) to give $N^4$-butyryl-2',3'-bis-O-(tert-butyldimethylsilyl)-5'-deoxy-5-fluorocytidine (15.32 g).

4(b) The product of Example 4(a) was treated in a manner analogous to that of Example 1(b) to give colorless crystals of $N^4$-butyryl-5'-deoxy-5-fluorocytidine.

The following compounds were obtained according to a manner analogous to that of Example 4:

| Example No. | R | Melting point °C. | Recrystallization solvent | MS |
|---|---|---|---|---|
| 5 | —CO(CH$_2$)$_6$CH$_3$ | 106~107 | Et$_2$O—MeOH | 372 (MH$^+$) |
| 6 | —CO(CH$_2$)$_7$CH$_3$ | (obtained as amorphous powder) | | 386 (MH$^+$) |
| 7 | —CO(CH$_2$)$_{14}$CH$_3$ | 65~66 | MeOH | 484 (MH$^+$) |
| 8 | —CO(CH$_2$)$_{16}$CH$_3$ | 65~66 | MeOH | 512 (MH$^+$) |
| 9 | —COCH(CH$_3$)$_2$ | (obtained as amorphous powder) | | 316 (MH$^+$) |
| 10 | —COC(CH$_3$)$_3$ | (obtained as amorphous powder) | | 330 (MH$^+$) |
| 11 | —CO-cyclopropyl | 168–170 | EtOAc—MeOH | 314 (MH$^+$) |
| 12 | —CO-cyclohexyl | (obtained as amorphous powder) | | 356 (MH$^+$) |
| 13 | —CO-adamantyl | (obtained as amorphous powder) | | 408 (MH$^+$) |
| 14 | —CO—CH$_2$—phenyl | (obtained as amorphous powder) | | 364 (MH$^+$) |
| 15 | —CO—CH=CH—phenyl | 169~171 | EtOAc | 376 (MH$^+$) |
| 16 | —CO—phenyl | 165~166 | EtOAc | 350 (MH$^+$) |
| 17 | —CO—C$_6$H$_4$—CH$_3$ (para) | 158~159 | MeOH | 363 (MH$^+$) |
| 18 | —CO—C$_6$H$_4$—CH$_3$ (meta) | 140~142 | EtOH | 364 (MH$^+$) |
| 19 | —CO—C$_6$H$_4$—CH$_3$ (ortho) | 187~190 | EtOH | 364 (MH$^+$) |
| 20 | —CO—C$_6$H$_4$—Cl (para) | 143~145 | EtOAc | 384 (MH$^+$) |

| Example No. | R | Melting point °C. | Recrystallization solvent | MS |
|---|---|---|---|---|
| 21 | —CO—C₆H₄—Cl (3-Cl) | 164~166 | EtOAc | 384 (MH⁺) |
| 22 | —CO—C₆H₄—Cl (2-Cl) | 182~184 (dec.) | MeOH | 384 (MH⁺) |
| 23 | —CO—C₆H₄—F (4-F) | 161~163 | MeOH | 368 (MH⁺) |
| 24 | —CO—C₆H₄—OCH₃ (4-OCH₃) | 166~167 | EtOAc | 379 (MH⁺) |
| 25 | —CO—C₆H₄—OCH₃ (2-OCH₃) | 161~163 | CH₂Cl₂ | 380 (MH⁺) |
| 26 | —CO—C₆H₃(OCH₃)₂ (3,4-diOCH₃) | 153~156 | MeOH | 410 (MH⁺) |
| 27 | —CO—C₆H₃(OCH₃)₂ (2,4-diOCH₃) | 159~161 | CH₂Cl₂—MeOH | 410 (MH⁺) |
| 28 | —CO—C₆H₃(OCH₃)₂ (2,5-diOCH₃) | 207~210 (dec.) | EtOH | 410 (MH⁺) |
| 29 | —CO—C₆H₄—NO₂ (4-NO₂) | 177~179 | CH₂Cl₂ | 395 (MH⁺) |
| 30 | —CO—C₆H₄—NO₂ (3-NO₂) | 177~178 | EtOAc | 395 (MH⁺) |
| 31 | —CO—C₆H₄—CO₂CH₃ (4-CO₂CH₃) | 193~194 | MeOH | 408 (MH⁺) |

-continued

| Example No. | R | Melting point °C. | Recrystallization solvent | MS |
|---|---|---|---|---|
| 32 | —CO—⟨C₆H₄⟩—SCH₃ | 155~158 | MeOH | 396 (MH+) |
| 33 | —CO—⟨pyridyl-N⟩ | 170~172 | EtOH | 351 (MH+) |
| 34 | —CO—⟨pyridyl-N⟩ | 155~157 | MeOH | 351 (MH+) |
| 35 | —CO—⟨pyridyl-N⟩ | 176~178 | EtOH | 351 (MH+) |
| 36 | —CO—⟨furyl-O⟩ | 177~179 | EtOH | 340 (MH+) |
| 37 | —CO—⟨thienyl-S⟩ | 181~183 | EtOH | 356 (MH+) |
| 38 | —CO—⟨N-CH₃ pyrrolyl⟩ | 155~156 | EtOAc | 353 (MH+) |
| 39 | —CO—⟨thienyl-S⟩-CH₃ | 171~175 | MeOH | 370 (MH+) |
| 40 | —CO—⟨naphthyl⟩ | 167~168 | CH₂Cl₂ | 400 (MH+) |
| 41 | —CO₂(CH₂)₇CH₃ | 107~109 | Et₂O | 402 (MH+) |
| 42 | —CO₂CH₂—⟨C₆H₅⟩ | 150~151 | MeOH | 380 (MH+) |

EXAMPLE 43

5'-Deoxy-5-fluorocytidine (735 mg) and butyric anhydride (1.04 g) was dissolved in 75% aqueous dioxane (20 ml). The mixture was stirred for 18 hours at room temperature. After removal of the solvent, the residue was purified by silica gel column chromatography to give colorless crystals of N⁴-butyryl-5'-deoxy-5-fluorocytidine (420 mg), mp 156°~157° C.; MS 316 (MH+).

EXAMPLE 44

(1) 5'-Deoxy-5-fluorocytidine (4.9 g) and trimethylsilyl chloride (5.58 ml) were dissolved in dry pyridine (50 ml). The mixture was stirred for 2 hours. To the reaction mixture was added ethyl chlorothioformate (2.09 ml). After stirring of the mixture for 2.5 hours pyridine was evaporated under reduced pressure. The residue was then partitioned between water and ethyl acetate. The organic layer was washed with water, dried over anhydrous sodium sulfate and concentrated under reduced pressure. To the residue were added citric acid (5 g) and methanol (80 ml). The mixture was stirred for 1 hour. After removal of the solvent under reduced pressure the residue was purified by silica gel column chromatography (methanol-dichloromethane) followed by recrystallization from dichloromethane to give 2.66 g of 5'-deoxy-N⁴-[(ethylthio)carbonyl]-5-fluorocytidine, mp 138°~139° C. (dec.); MS 334 (MH+).

(2)(a) To a stirred solution of 5'-deoxy-5-fluoro-2',3'-O-isopropylidenecytidine (1 g) obtained in Reference example (b) in pyridine (8 ml) was added ethyl chlorothioformate (365 μl) at 0° C., and the mixture was stirred at room temperature overnight. The reaction mixture was concentrated under reduced pressure and the residue was partitioned between ethyl acetate and water. The organic layer was washed with sodium hydrogen carbonate solution and water, and dried over anhydrous sodium sulfate. After removal of the solvent the residue was purified by silica gel column chromatography (CHCl₃) to give 5'-deoxy-$N^4$-[(ethylthio)carbonyl]-5-fluoro-2',3'-O-isopropylidenecytidine (510 mg), MS 374 (MH+).

(b) To a solution of the product of Example 44(2)(a) (150 mg) in 50% aqueous ethanol was added Dowex 50 (H+) (150 mg), and the mixture was heated at 50°~60° C. with stirring for 4 hours. Dowex 50 was filtered off and the filtrate was concentrated to dryness under reduced pressure. The residue was purified by silica gel column chromatography (CHCl₃-acetone) followed by recrystallization from dichloromethane to give 5'-[(ethylthio)carbonyl]-5-fluorocytidine; mp 138°~139° C. (dec.). MS 334 (MH+).

The following compounds were obtained according to a manner analogous to that of Example 44 (1):

| Example No. | R | Melting point °C. | Recrystallization solvent | MS |
|---|---|---|---|---|
| 45 | —COCH₂CH₃ | 119~120 | EtOAc—Et₂O | 302 (MH+) |
| 46 | —CO(CH₂)₃CH₃ | 150~151 | EtOAc | 330 (MH+) |
| 47 | —COCH₂CH(CH₃)₂ | 142~143 | EtOAc | 330 (MH+) |

EXAMPLE 48

A solution of piperonylic acid (0.42 g) in dry acetonitrile (5 ml) containing triethylamine (0.36 ml) was treated with diethyl chlorophosphate (0.37 ml) for 1 hour. To the reaction mixture were added 2',3'-bis-O-(tert-butyldimethylsilyl)-5'-deoxy-5-fluorocytidine (1.0 g) obtained in Reference example (a), triethylamine (0.36 ml) and 4-dimethylaminopyridine (0.05 g). After stirring of the mixture for 12 hours at room temperature, acetonitrile was evaporated under reduced pressure. The residue was partitioned between water and ether. The organic layer was washed with water, dried over anhydrous sodium sulfate and concentrated under reduced pressure. The obtained powder was dissolved in tetrahydrofuran (6.3 ml) containing tetrabutylammonium fluoride (1.65 g) and the reaction mixture was stirred for 1 hour. After removal of the solvent under reduced pressure, the residue was purified by silica gel column chromatography (isopropanol-dichloromethane) followed by recrystallization from ethyl acetate to give 0.5 g of 5'-deoxy-5-fluoro-$N^4$-piperonyloylcytidine, mp 124°~125° C.: MS 394 (MH+).

The following compound was obtained according to a manner analogous to that of Example 48:

| Example No. | R | Melting point °C. | Recrystallization solvent | MS |
|---|---|---|---|---|
| 49 | —COCH₂CH=CH₂ | 137~138 | EtOAc | 314 (MH+) |

EXAMPLE 50

3-Furoic acid (0.355 g) and 2,4,6-triisopropyl benzene-sulfonyl chloride (0.96 g) were dissolved in dry pyridine (5 ml). The mixture was stirred for 1 hour. To the mixture were added 2',3'-bis-O-(tert-butyldimethylsilyl)-5'-deoxy-5-fluorocytidine (1.0 g) obtained in Reference example (a) and 4-dimethylaminopyridine (0.80 g). After stirring of the mixture for 12 hours at room temperature. pyridine was evaporated under reduced pressure. The residue was then treated as in Example 48 to give 0.55 g of 5'-deoxy-5-fluoro-$N^4$-(3-furoyl)cytidine, mp 173°~174° C. (ethanol); MS 340 (MH+).

The following compounds were obtained according to a manner analogous to that of Example 50:

| Example No. | R | Melting point °C. | Recrystallization solvent | MS |
|---|---|---|---|---|
| 51 | —COCH₂—⟨C₆H₄⟩—OCH₃ | (obtained as amorphous powder) | | 394 (MH+) |
| 52 | —CO(CH₂)₂—⟨C₆H₅⟩ | 146~148 | EtOH | 378 (MH+) |
| 53 | —CO—⟨C₆H₃⟩(CH₃)(CH₃) | 161~162 | EtOH | 378 (MH+) |
| 54 | —COCH₂—(indol-3-yl) | (obtained as amorphous powder) | | 403 (MH+) |

-continued

| Example No. | R | Melting point °C. | Recrystallization solvent | MS |
|---|---|---|---|---|
| 55 | —CO-[furan-NO2] | 162~163 | EtOH | 385 (MH+) |
| 56 | —CO-[phenyl]-COCH3 | 176~178 | EtOAc | 392 (MH+) |

EXAMPLE 57

(a) To a stirred solution of 5'-deoxy-5-fluorouridine (24.6 g) in dry pyridine (150 ml) was added dropwise 24.5 ml of benzoyl chloride over 10 minutes at 0° C. and the mixture was stirred for 5 hours at room temperature. After removal of pyridine under reduced pressure the residue was partitioned between water and ethyl acetate. The organic layer was washed with saturated sodium hydrogen carbonate solution and water, dried over anhydrous sodium sulfate and concentrated under reduced pressure. The residue was recrystallized from ethyl acetate - n-hexane to give 38.9 g of 2',3'-di-O-benzoyl-5'-deoxy-5-fluorouridine, MS 455 (MH+).

(b) To a mixture of N-methylimidazole (0.8 ml) and phosphoryl chloride (0.28 ml) in acetonitrile (20 ml) was added 2',3'-di-O-benzoyl-5'-deoxy-5-fluorouridine (500 mg) obtained above at 0° C. After stirring of the reaction mixture for 1.5 hours at room temperature 28% ammonium hydroxide (2.5 ml) was added to the mixture at 0° C., and the mixture was stirred for 1 hour at room temperature. Acetonitrile and ammonia were removed under reduced pressure. The residue was acidified with 1N-HCl and then extracted with ethyl acetate. The organic layer was washed with water, dried over anhydrous sodium sulfate and concentrated under reduced pressure. The residue was recrystallized from ethyl acetate to give 155 mg of 2',3'-di-O-benxoyl- 5'-deoxy-5-fluorocytidine, mp 192°~194° C.; MS 476 ((M+Na)+).

EXAMPLE 58

(a) To ice cooled acetic anhydride (0.57 ml) was added dropwise 99% formic acid (286 µl). The solution was stirred for 15 minutes at 0° C. and for 50 minutes at 50° C., and then cooled to 0° C. To the solution was added 2',3'-bis-O-(tert-butyldimethylsilyl)-5'-deoxy-5-fluorocytidine (473 mg) obtained in Reference example (a) in dry pyridine (5 ml) at 0° C. The reaction mixture was stirred for 10 minutes at 0° C. and for 26 hours at room temperature. After removal of the solvent under reduced pressure the residue was partitioned between water and ethyl acetate. The organic layer was washed with saturated sodium hydrogen carbonate solution and water, and dried over anhydrous sodium sulfate. Ethyl acetate was evaporated under reduced pressure and the residue was purified by silica gel column chromatography (n-hexane - ethyl acetate) followed by recrystallization from n-hexane - ethyl acetate to give 144 mg of 2',3'-bis-O-(tert-butyldimethylsilyl)-5'-deoxy-5-fluoro-N4-formylcytidine, mp 188° C. (dec.); MS 502 (MH+).

(b) The product of Example 58(a) was treated in a manner analogous to that of Example 1 (b) to give amorphous powder of 5'-deoxy-5-fluoro-N4-formylcytidine, MS 274 (MH+).

EXAMPLE 59

5'-Deoxy-5-fluorocytidine (245 mg) was dissolved in dry pyridine (5 ml). To the solution was added benzoyl chloride (130 µl) with stirring at 0° C. The reaction mixture was stirred for 1 hour at 0° C. After removal of the solvent under reduced pressure, the residue was purified by silica gel column chromatography (dichloromethane - methanol) followed by recrystallization from ethyl acetate to give colorless crystals of 3'-O-benzoyl-5'-deoxy-5-fluorocytidine (51 mg). mp 127°~129° C.; MS 350 (MH+).

EXAMPLE 60

35 mg of the product of Example 59 was dissolved in dry pyridine (0.5 ml). To the solution was added trimethylsilyl chloride (13.8 µl). After stirring for 2 hours at room temperature, benzoyl chloride (12.6 µl) was added. The reaction mixture was stirred for 1 hour. After removal of the solvent under reduced pressure, the residue was dissolved in dry methanol (0.5 ml). To the solution was added potassium carbonate (15 mg) and the reaction mixture was stirred for 30 minutes at 0° C. After removal of the solvent under reduced pressure, the residue was partitioned between water and ethyl acetate. The organic layer was dried over anhydrous magnesium sulfate and concentrated under reduced pressure. The residue was purified by silica gel column chromatography (dichloromethane - methanol) to give 15 mg of amorphous powder of N4,3'-O-dibenzoyl-5'-deoxy-5-fluorocytidine, MS 454 (MH+).

EXAMPLE 61

5'-Deoxy-5-fluorocytidine (245 mg), benzoyl chloride (400 µl) and 4-dimethylaminopyridine (122 mg) were dissolved in dry pyridine (5 ml). After stirring for 3 hours at room temperature pyridine was removed under reduced pressure. The residue was partitioned between ethyl acetate and water. The ethyl acetate layer was dried over magnesium sulfate and concentrated under reduced pressure. The residue was recrystallized from methanol to give N4,2'-O,3'-O-tribenzoyl-5'-deoxy-5-fluorocytidine (280 mg), mp 158°~160° C.; MS 558 (MH+).

The following Examples illustrate pharmaceutical preparations containing a compound provided by the present invention.

EXAMPLE A

Interlocking gelatin capsules each containing the following ingredients were manufactured in a manner known per se:

| | |
|---|---|
| N⁴-Butyryl-5'-deoxy-5-fluorocytidine | 100 mg |
| Corn starch | 20 mg |
| Titanium dioxide | 385 mg |
| Magnesium stearate | 5 mg |
| Film | 20 mg |
| PEG 6000 | 3 mg |
| Talc | 10 mg |
| | 543 mg |

EXAMPLE B

Tablets each containing the following ingredients were manufactured in a manner known per se:

| | |
|---|---|
| N⁴-Butyryl-5'-deoxy-5-fluorocytidine | 100 mg |
| Lactose | 25 mg |
| Corn starch | 20.2 mg |
| Hydroxypropylmethyl cellulose | 4 mg |
| Magnesium stearate | 0.8 mg |
| Film | 10 mg |
| PEG 6000 | 1.5 mg |
| Talc | 4.5 mg |
| | 166 mg |

EXAMPLE C

Dry parenteral dosage forms were manufactured in a manner known per se:

(1) A total 5 g of N⁴-butyryl-5'-deoxy-5-fluorocytidine was dissolved in 75 ml of distilled water. the solution was subjected to a bacteriological filtration, and then divided aseptically into 10 sterile vials. The solution was then freeze-dried to yield 500 mg of sterile dry solid per vial.

(2) Clean N⁴-butyryl-5'-deoxy-5-fluorocytidine in the amount of 500 mg per vial or ampoule was sealed in the receptacle and heat-sterilized.

The above dry dosage forms were reconstituted before use by adding a suitable sterile aqueous solvent such as water for injection or isotonic sodium chloride or 5% dextrose for parenteral administration.

What we claim is:

1. A compound of the formula:

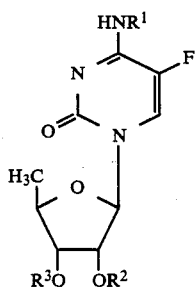

wherein $R^1$, $R^2$ and $R^3$ are each independently hydrogen, or an easily hydrolyzable radical under physiological conditions, with the proviso that, at least one of $R^1$, $R^2$, or $R^3$ is an easily hydrolyzable radical under physiological conditions;
as well as hydrates or solvates of the compounds of the general formula (I).

2. The compound of claim 1 wherein the easily hydrolyzable radical is selected from the group consisting of $R^4CO—, R^5OCO—,$ or $R^6SCO—$ wherein $R^4$ represents hydrogen, alkyl, cycloalkyl, oxoalkyl, alkenyl, aralkyl or aryl; $R^5$ is alkyl or aralkyl radical; and $R^6$ is alkyl or aralkyl.

3. A compound selected from the group consisting of:
N⁴-acetyl-5'-deoxy-5-fluorocytidine,
5'-deoxy-5-fluoro-N⁴-propionylcytidine,
N⁴-butyryl-5'-deoxy-5-fluorocytidine,
5'-deoxy-5-fluoro-N⁴-isobutyrylcytidine,
5'-deoxy-5-fluoro-N⁴-(2-methylbutyryl)cytidine,
5'-deoxy-N⁴-(2-ethylbutyryl)-5-fluorocytidine,
5'-deoxy-N⁴-(3,3-dimethylbutyryl)-5-fluorocytidine,
5'-deoxy-5-fluoro-N⁴-pivaloylcytidine,
5'-deoxy-5-fluoro-N⁴-valerylcytidine,
5'-deoxy-5-fluoro-N⁴-isovalerylcytidine,
5'-deoxy-5-fluoro-N⁴-(2-methylvaleryl)cytidine,
5'-deoxy-5-fluoro-N⁴-(3-methylvaleryl)cytidine,
5'-deoxy-5-fluoro-N⁴-(4-methylvaleryl)cytidine,
5'-deoxy-5-fluoro-N⁴-hexanoylcytidine,
5'-deoxy-5-fluoro-N⁴-heptanoylcytidine,
5'-deoxy-5-fluoro-N⁴-octanoylcytidine,
5'-deoxy-5-fluoro-N⁴-nonanoylcytidine,
5'-deoxy-5-fluoro-N⁴-hexadecanoylcytidine,
N⁴-benzoyl-5'-deoxy-5-fluorocytidine,
5'-deoxy-5-fluoro-N⁴-(4-methylbenzoyl)cytidine,
5'-deoxy-5-fluoro-N⁴-(3-methylbenzoyl)cytidine,
5'-deoxy-5-fluoro-N⁴-(2-methylbenzoyl)cytidine,
5'-deoxy-N⁴-(4-ethylbenzoyl)-5-fluorocytidine,
5'-deoxy-N⁴-(3,4-dimethylbenzoyl)-5-fluorocytidine,
5'-deoxy-N⁴-(3,5-dimethylbenzoyl)-5-fluorocytidine,
5'-deoxy-5-fluoro-N⁴-(4-methoxybezoyl)cytidine,
5'-deoxy-N⁴-(3,4-dimethoxybenzoyl)-5-fluorocytidine,
5'-deoxy-N⁴-(3,5-dimethoxybenzoyl)-5-fluorocytidine,
5'-deoxy-5-fluoro-N⁴-(3,4,5-trimethoxybenzoyl)cytidine,
5'-deoxy-5-fluoro-N⁴-(3,4,5-triethoxybenzoyl)cytidine,
5'-deoxy-N⁴-(4-ethoxybenzoyl)-5-fluorocytidine,
5'-deoxy-5-fluoro-N⁴-(4-propoxybenzoyl)cytidine,
5'-deoxy-N⁴-(3,5-diethoxybenzoyl)-5-fluorocytidine,
N⁴-(4-chlorobenzoyl)-5'-deoxy-5-fluorocytidine,
5'-deoxy-N⁴-(3,4-dichlorobenzoyl)-5-fluorocytidine,
5'-deoxy-N⁴-(3,5-dichlorobenzoyl)-5-fluorocytidine,
5'-deoxy-5-fluoro-N⁴-(4-nitrobenzoyl)cytidine,
5'-deoxy-5-fluoro-N⁴-(4-methoxycarbonylbenzoyl)cytidine,
N⁴-(4-acetylbenzoyl)-5'-deoxy-5-fluorocytidine,
5'-deoxy-5-fluoro-N⁴-(phenylacetyl)cytidine,
5'-deoxy-5-fluoro-N⁴-(4-methoxyphenylacetyl)cytidine,
5'-deoxy-5-fluoro-N⁴-nicotinoylcytidine,
5'-deoxy-5-fluoro-N⁴-isonicotinoylcytidine
5'-deoxy-5-fluoro-N⁴-picolinoylcytidine,
5'-deoxy-5-fluoro-N⁴-(2-furoyl)cytidine,
5'-deoxy-5-fluoro-N⁴-(5-nitro-2-furoyl)cytidine,
5'-deoxy-5-fluoro-N⁴-(2-thenoyl)cytidine,
5'-deoxy-5-fluoro-N⁴-(5-methyl-2-thenoyl)cytidine,
5'-deoxy-5-fluoro-N⁴-(1-methyl-2-pyrrolecarbonyl)cytidine,
5'-deoxy-5-fluoro-N⁴-(3-indolylacetyl)cytidine,
N⁴-(3-butenoyl)-5'-deoxy-5-fluorocytidine,
3'-0-benzoyl-5'-deoxy-5-fluorocytidine,
N⁴,3'-0-dibenzoyl-5'-deoxy-5-fluorocytidine and
5'-deoxy-N⁴-(ethylthio)carbonyl-5-fluorocytidine.

4. A compound of claim 2 selected from the group consisting of:
5'-deoxy-5-fluoro-N⁴-octadecanoylcytidine,
N⁴-cyclopropanecarbonyl-5'-deoxy-5-fluorocytidine,
N⁴-cyclohexanecarbonyl-5'-deoxy-5-fluorocytidine, N4-(1-adamantanecarbonyl)-5'-deoxy-5-fluorocytidine, 5'-deoxy-5-fluoro-N4-(2-methoxybenzoyl)cytidine, 5'-deoxy-N4-(2,4-dimethoxybenzoyl)-5-fluorocytidine, 5'-deoxy-5-fluoro-N4-piperonyloylcytidine, 5'-deoxy-5-fluoro-N4-(4-fluorobenzoyl)cytidine, N4-(2-chlorobenzoyl)-5'-deoxy-5-fluorocytidine, N4-(3-chlorobenzoyl)-5'-deoxy-5-fluorocytidine, 5'-deoxy-5-fluoro-N4-(3-nitrobenzoyl)cytidine, 5'-deoxy-5-fluoro-N4-[4-(methylthio)benzoyl]cytidine, 5'-deoxy-5-fluoro-N4-(2-naphthoyl)cytidine, 5'-deoxy-5-fluoro-N4-(3-furoyl)cytidine, 5'-deoxy-5-fluoro-N4-(3-phenylpropionyl)cytidine, N4-cinnamoyl-5'-deoxy-5-fluorocytidine, 2',3'-di-0-benzoyl-5'-deoxy-5-fluorocytidine, N4,2'-0,3'-0-tribenzoyl-5'-deoxy-5-fluorocytidine, 5'-deoxy-5-fluoro-N4-(octyloxycarbonyl)cytidine, N4-(benzyloxycarbonyl)-5'-deoxy-5-fluorocytidine and 5'-deoxy-5-fluoro-N4-formylcytidine.

5. A method for inhibiting the growth of sarcoma, fibrosarcoma, or carcinoma in a subject comprising administering to the subject an antitumor effective amount of the compound of Formula I or the hydrates and solvates thereof.

6. A method for the manufacture of the compound of Formula I comprising reacting a compound of the formula

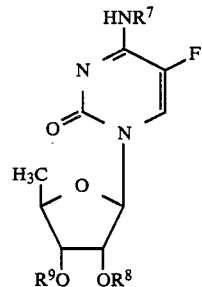

wherein $R^7$ represents hydrogen or an amino-protecting radical; $R^8$ and $R^9$ are each independently hydrogen, or a hydroxy-protecting group; or $R^8$ and $R^9$, taken together, form a cyclic hydroxy-protecting group, with a compound of the formula

XCOR⁴ (III)

wherein X is a leaving radical and $R^4$ is hydrogen, alkyl, cycloalkyl, oxoalkyl, alkenyl, aralkyl, or aryl; or with a compound of the formula

YCOR¹⁰ (IV)

wherein Y is halogen and $R^{10}$ is a radical of the formula,

R⁵ZO—, or R⁶S— wherein $R^5$ is alkyl or aralkyl, and $R^6$ is alkyl or aralkyl; followed, if necessary, by removal of a protecting radical.

7. A pharmaceutical composition with antisarcoma, antifibrosarcoma, or anticarinoma activity comprised of an therapeutically effective amount of a compound of Formula I as the active ingredient.

* * * * *

UNITED STATES PATENT AND TRADEMARK OFFICE

CERTIFICATE EXTENDING PATENT TERM
UNDER 35 U.S.C. § 156

PATENT NO.      :   4,966,891

ISSUED          :   October 30, 1990

INVENTORS       :   Morio Fujiu, et al.

PATENT OWNER    :   Hoffman-La Roche, Inc.

PRODUCT         :   Xeloda™ (capecitabine)

This is to certify that an application under 35 U.S.C. § 156 has been filed in the U.S. Patent and Trademark Office, requesting extension of the term of U.S. Patent No. 4,966,891 based upon the regulatory review of the product Xeloda™ (capecitabine) by the Food and Drug Administration. Since it appears that the requirements of the law have been met, this certificate extends the term of the patent for the period of 796 days from November 8, 2008, the original expiration date of the patent, subject to the provisions of 35 U.S.C. § 41(b), with all rights pertaining thereto as provided by 35 U.S.C. § 156(b).

I have caused the seal of the U.S. Patent and Trademark Office to be affixed this 12th day of September 2000.

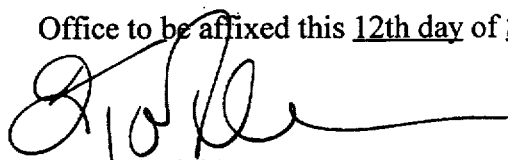

Q. Todd Dickinson
Under Secretary of Commerce for Intellectual Property
and Director of the United States Patent and
Trademark Office